US012779146B2

(12) United States Patent
Grundmann et al.

(10) Patent No.: US 12,779,146 B2
(45) Date of Patent: Nov. 3, 2026

(54) INSUFFLATION DEVICE WITH PROTECTION MODE

(71) Applicant: Novanta Medical GmbH, Berlin (DE)

(72) Inventors: Julia Grundmann, Berlin (DE); Matthias Hildebrand, Berlin (DE)

(73) Assignee: Novanta Medical GmbH, Berlin (DE)

( * ) Notice: Subject to any disclaimer, the term of this patent is extended or adjusted under 35 U.S.C. 154(b) by 653 days.

(21) Appl. No.: 18/137,043

(22) Filed: Apr. 20, 2023

(65) Prior Publication Data

US 2024/0001050 A1 Jan. 4, 2024

Related U.S. Application Data

(60) Provisional application No. 63/337,327, filed on May 2, 2022.

(30) Foreign Application Priority Data

Apr. 21, 2022 (DE) ......................... 102022001374.6

(51) Int. Cl.
*A61M 13/00* (2006.01)
*A61M 39/22* (2006.01)

(52) U.S. Cl.
CPC ............ *A61M 13/00* (2013.01); *A61M 39/22* (2013.01); *A61M 2205/3331* (2013.01); *A61M 2205/502* (2013.01)

(58) Field of Classification Search
CPC ... A61M 13/00; A61M 13/003; A61M 13/006
See application file for complete search history.

(56) References Cited

U.S. PATENT DOCUMENTS

| | | | | |
|---|---|---|---|---|
| 5,439,441 A * | 8/1995 | Grimsley | A61M 13/003 | 600/561 |
| 2006/0129087 A1 * | 6/2006 | Uesugi | A61M 13/003 | 604/118 |
| 2010/0114011 A1 | 5/2010 | Herrmann | | |
| 2012/0130304 A1 * | 5/2012 | Barish | A61M 13/003 | 604/24 |
| 2016/0262600 A1 * | 9/2016 | Yamaoka | A61M 13/003 | |
| 2021/0290864 A1 * | 9/2021 | Yamaoka | A61M 13/003 | |

OTHER PUBLICATIONS

Examination Report Excerpt of Priority DE 10202001374.6 (no date).

* cited by examiner

*Primary Examiner* — Andrew H Nguyen
(74) *Attorney, Agent, or Firm* — McCarter & English, LLP; David J. Silvia

(57) ABSTRACT

The present invention relates to an insufflator with a novel type of input processing for the setpoint value of the pressure in the body cavity. The new device makes it possible to predefine the pressure in the body cavity as the set pressure when there is sufficient expansion and to apply this pressure to the previous control in order to work as gently as possible on the patient.

7 Claims, 1 Drawing Sheet

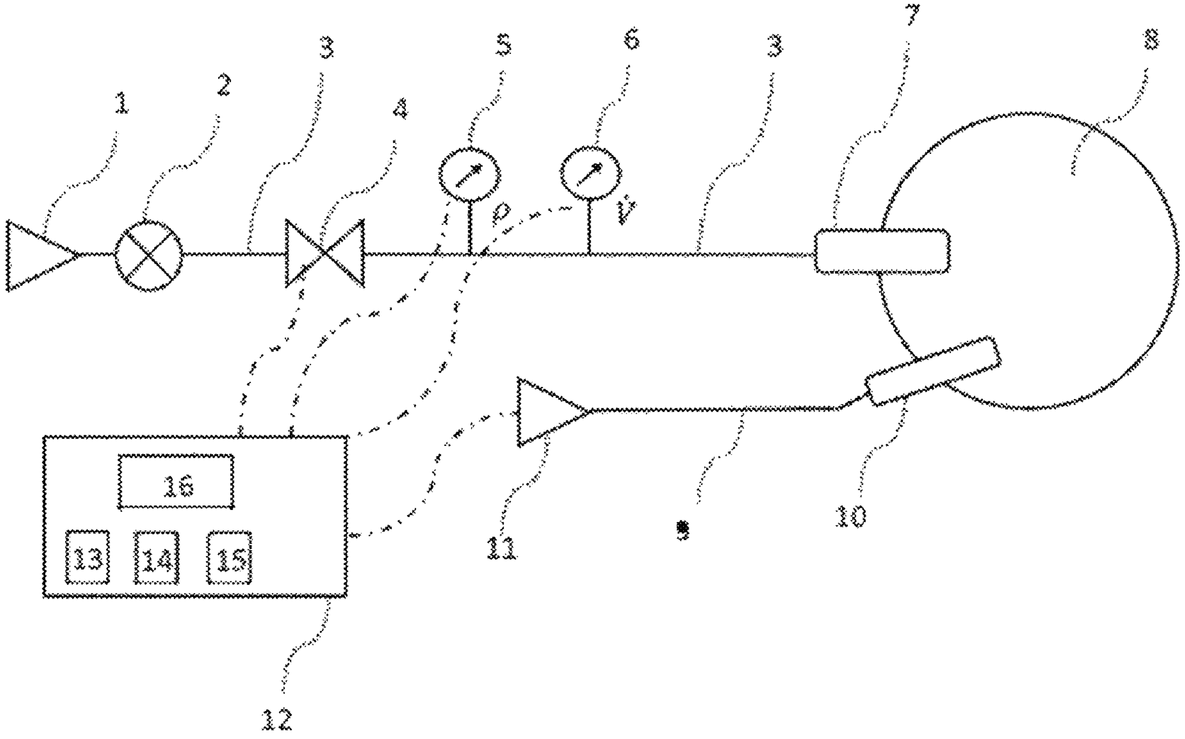
1
2
3
4
5
6
3
7
8
p
V
16
13
14
15
12
11
9
10

INSUFFLATION DEVICE WITH PROTECTION MODE

CROSS REFERENCE TO RELATED APPLICATIONS

This application claims priority from German Patent Application No. 102022001374.6 filed on Apr. 21, 2022, the entire disclosure of which is incorporated herein by reference.

BACKGROUND OF THE INVENTION

1. Field of the Invention

The present invention relates to an insufflator with a novel type of input processing for the setpoint value of the pressure in the body cavity. The new device makes it possible to predefine the pressure in the body cavity as the set pressure when there is sufficient expansion and to apply this pressure to the previous control in order to work as gently as possible on the patient.

2. Background and State of the Art

Insufflators are known from the prior art in manifold configurations. Insufflators usually comprise a tube through which a medical gas is introduced into a body cavity (for example, an abdomen). The gas creates a positive pressure that expands the body cavity to provide sufficient space for the visual inspection or alternatively the therapeutic intervention or the medical procedure. Optional embodiments allow for the evacuation of the gas from the body cavity by means of a second tube. Such embodiments are used, in particular, for therapeutic interventions carried out using electrosurgery or lasers in order to remove and to filter smoke gases that are harmful to health, as well as to ensure visibility during the intervention.

In practice, it has proven difficult to minimize the pressure in the body cavity in a patient-dependent manner over the course of the entire procedure. By means of a minimal increase in pressure, as would in any event correspond to the natural situation, an overburdening or injury to structures in the body cavity is precluded and can even prevent negative effects on the blood pressure of the patient brought about by the pressure in the body cavity.

At the same time, the necessary expansion must take place in order to be able to carry out the procedure without disproportionate effort on the part of the surgeon and risk due to instrument movements or lack of visibility of the patient.

The requirement to introduce as little pressure as possible through the expansion medium and at the same time to create the necessary space for movement and visibility in order to be able to carry out the medical procedure is usually achieved by setting a preset or set pressure for the control system in the insufflator.

A patient-specific setting requires a great deal of time on the part of the surgeon or operator through trial and error to find the optimum setpoint value. Alternatively, the surgeon must contribute their experience, such that a wide range of influences affects the safe assessment and ultimately does not guarantee reliable protection of the body of the patient.

The method of achieving minimum expansion by simply introducing a small amount of expansion medium is not expedient, since expansion medium is constantly lost due to changes of instruments and leakage, and to refill an adequate quantity for a simple introduction of medium is tied to much effort for the operator. Therefore, it is common to use a control for the amount of expansion medium in the body cavity, wherein the manipulated variable is traditionally the pressure in the body cavity (EP3049136B1).

A specification based on the selection in the device of so-called indications, which is to say default settings, as to whether the patient is an overweight person, an athletic person with firm connective tissue or a child, can only preset the setpoint values in broad categories.

The situation becomes complicated if not only an expansion but also an evacuation is to take place during the medical procedure. In this case, the task of pressure control for the body cavity is to compensate for leakage and avoid positive pressure. Since the aspirated expansion medium is usually returned through a filter, a pump is included in the evacuation circuit or alternatively the smoke evacuation circuit, which represents a second actuator in the control system, whereas the smoke gas filter provides a further disturbance variable, among others through its variable permeability over time. For this purpose, a slightly higher set pressure is typically accepted.

Configurations in which the set pressure can be increased or reduced in steps by means of the user interface of the device have therefore become established.

SUMMARY OF THE INVENTION

In order to overcome the above-mentioned disadvantages of previous set pressure specifications, the task has arisen of providing an input possibility which applies a setpoint value in the control system of the insufflator without input errors or additional effort.

The present invention therefore relates to an insufflator for the minimally invasive insufflator for minimally invasive surgery, comprising a gas connection (1) with a proportional valve (2), one first trocar (7) one gas supply line (3) for gas from the gas connection (1 with pressure measurement (5), filter (not shown) and connection to the first trocar (7) for insufflating gas into a cavity (8), wherein the gas flow is controllable by a mass flow controller (4) in the range 0-50 L/min. Optionally at least one gas flow sensor (6) is included that is adapted to determine the gas flow into the cavity (8). Also included is at least one pressure sensor (5) that is adapted to determine the pressure in the cavity, optionally one evacuation device (11) with adjustable evacuation capacity, one second trocar (10) for the outlet of gas from the cavity (8), optionally with evacuation hose (9), connected to the evacuation device (11) with adjustable evacuation capacity, and one electronic control unit with at least one memory for storing at least one first set pressure and one second set pressure, Lastly, also included is one first input device (12), one second input device (13) and one display device (16). Wherein the electronic control unit carries out the control of the pressure in the cavity (8) by changing the gas inflow, wherein a first set pressure in the cavity (8) is preset before the start of the insufflation by means of the first input device (12) of the electronic control unit. Wherein by actuating the second input device (13) before the first set pressure of the electronic control unit is reached, the pressure prevailing at the time of actuation of the second input device can be preset as the second set pressure. Wherein the second set pressure is maintained by the electronic control unit for further insufflation.

Further embodiments of the invention, including the associated operating methods, are described below and are partly the subject matter of subsidiary claims and subclaims.

BRIEF DESCRIPTION OF THE FIGURES

The invention is illustrated in principle in FIG. 1.

DETAILED DESCRIPTION OF PREFERRED EMBODIMENTS

The invention comprises a method to slowly increase the pressure in the body cavity (8 and to react to a suitable input by applying the currently achieved value as the set pressure value in the control system of the insufflator. Typically, the electronic control unit will set as high a gas flow as possible at the start of the insufflation in order to reach the set pressure that is first set as quickly as possible.

In the novel gentle mode, the user stops the expansion as soon as it is large enough to carry out the medical procedure. The method provides for the slow increase of the pressure in the body cavity (8) while waiting for a suitable input. This allows the user to determine the optimum expansion for the specific case and at the same time ensures that the body cavity is only expanded as far as is absolutely necessary. This pressure value (set pressure) confirmed by the input thus becomes the new standard setpoint value for this medical procedure. Moreover, the pressure value may be changed at any time, as described in the prior art.

If there is no input, which is to say the expansion is not actively influenced, the set pressure provided in the device for the selected indication is used as before. If no indication can be selected in the device, the set pressure provided or last selected is applied in the control system. The appropriate input is usually made by means of a query/input on the connected operator interfaces. Further options for the setting of parameters (amongst other also the set pressure) include input from a white balance button on the camera head, by means of a foot pedal, by means of voice control as well as by means of other input devices or alternatively remote controls connected to the device.

Traditionally, the gas flow is set as high as possible at the start of the insufflation so that the preparation for surgery does not take too long. The initial insufflation can occur with a gas flow of 3 L/min in adult patients. The planned pressure in the cavity (for example, abdomen) is approximately 15 mmHg. The planned pressure is reached after approx. 1 minute with the specified gas flow (cavity volume 3 L at 15 mmHg).

For smaller cavities (for example, rectum), the initial gas flow is 3 L/min. The planned pressure of 12 mmHg is reached after approx. 4 s (cavity volume 200 ml at 12 mmHg).

In further embodiments of the invention, after an initial expansion has occurred, the same method is used to correct the expansion.

For this purpose, a sequence is started in which no medical procedure is carried out and the pressure in the body cavity is initially reduced by a defined value, or the same method is used to reduce the pressure until an input is received. Here too, if no input is received, the limit is a value set in the device.

Subsequently, the pressure in the body cavity is slowly increased until the user gives an input making use of the possibilities already described above. If there is no input, the value stored in the device—as already described above—is used.

In a further embodiment, the sequence is started without reducing the pressure beforehand.

In a further embodiment, the pressure is likewise increased during smoke gas evacuation with or without prior reduction of the body cavity pressure, and the value determined by the input is defined as the set pressure for the smoke gas evacuation mode, and after shutdown, the set pressure last selected for the normal mode is used again for control. In this case, the increase in pressure up to the new set pressure can be made more slowly, which is to say with a lower gas flow, for example, with a gas flow that is 75%, 50% or 25% of the initial gas flow.

All of these combinations are considered to be inventive and provide a simple method to allow an adjustment of the set pressure value by the operator, who usually also performs the medical procedure, without excessive interaction with persons outside the sterile area, for maximum patient protection.

The reference signs used in FIG. 1 have the following meaning:

(1) Gas connection
(2) Proportional valve
(3) Gas supply line
(4) Volume flow control
(5) Pressure sensor
(6) Volume flow sensor (optional)
(7) First trocar
(8) Cavity
(9) Evacuation hose
(10) Second trocar
(11) Evacuation device with adjustable evacuation capacity
(12) First input device
(13) Second input device
(14) Third input device
(15) Actuating device (optional)
(16) Display device The invention also comprises methods of operating an insufflator as summarized below, in particular, a method of operating an insufflator for minimally invasive surgery, wherein the insufflator comprises a) a gas connection with a proportional valve;
b) one first trocar;
c) one gas supply line for gas from the gas connection with pressure measurement, filter and connection to the first trocar for insufflating gas into a cavity, wherein the gas flow is controllable by a mass flow controller in the range 0-50 L/min;
d) optionally at least one gas flow sensor adapted to determine the gas flow into the cavity;
e) at least one pressure sensor that is adapted to determine the pressure in the cavity;
f) optionally an evacuation device with adjustable evacuation capacity;
g) one second trocar for the outlet of gas from the cavity, optionally with evacuation hose, connected to the evacuation device with adjustable evacuation capacity;
h) one electronic control unit with at least one memory for storing at least one first set pressure and one second set pressure;
i) one first input device;
j) one second input device; and
k) one display device.

Wherein the method comprises that the electronic control unit undertakes the control of the pressure in the cavity by changing the inflow of gas. Wherein a first set pressure in the cavity is preset before the start of the insufflation by means of the first input device of the electronic control unit. Wherein the medical personnel, by actuating the second input device before the first set pressure of the electronic control unit is reached, can preset the pressure prevailing at the time of actuation of the second input device as the second set pressure. Wherein the second set pressure is maintained by the electronic control unit for further insufflation.

Method of operating an insufflator as recited above wherein the electronic control unit adjusts the first set pressure by changing the gas flow by renewed actuation of the second input device in the cavity.

The invention claimed is:

1. Insufflator for minimally invasive surgery, comprising
a) a gas connection with a proportional valve;
b) one first trocar;
c) one gas supply line for gas from the gas connection with pressure measurement and connection to the first trocar for insufflating gas into a cavity, wherein a gas flow is controllable by a mass flow controller in the range of 0-50 L/min;
d) optionally at least one gas flow sensor adapted to determine the gas flow into the cavity;
e) at least one pressure sensor that is adapted to determine a pressure in the cavity;
f) optionally an evacuation device with adjustable evacuation capacity;
g) one second trocar for evacuating gas from the cavity, optionally with an evacuation hose, connected to the evacuation device with adjustable evacuation capacity;
h) one electronic control unit with at least one memory for storing at least one first set pressure and one second set pressure;
i) one first input device;
j) one second input device;
k) one display device,
wherein the electronic control unit carries out a control of the pressure in the cavity by changing the gas flow through the gas supply line,
wherein the at least one first set pressure in the cavity is preset before a start of insufflation by means of the first input device of the electronic control unit,
wherein the electronic control unit is configured to increase the pressure in the cavity toward the at least one first set pressure, and
wherein, in response to an actuation of the second input device occurring before the at least one first set pressure of the electronic control unit is reached, the electronic control unit is configured to capture a pressure prevailing at the time of actuation of the second input device as the second set pressure, and
wherein the second set pressure is maintained by the electronic control unit for further insufflation.

2. The insufflator according to claim 1, wherein the electronic control unit adjusts the second set pressure in response to a renewed actuation of the second input device.

3. The insufflator according to claim 2, whereby the gas flow after renewed actuation of the second input device is 1-2.5 L/min.

4. The insufflator according to claim 1, wherein the electronic control unit comprises a third input device,
wherein the electronic control unit reduces the pressure in the cavity in response to an actuation of the third input device,
wherein the electronic control unit is further configured to capture the pressure prevailing at the time of the actuation of the second or the third input device as a third set pressure in response to a renewed actuation of the second or third input device,
wherein the third set pressure is maintained by the electronic control unit for further insufflation.

5. The insufflator according to claim 4, wherein the second or the third input device is selected from:
a white balance button on a camera head,
foot pedal,
voice control,
remote control.

6. The insufflator according to claim 1, wherein the gas flow at the start of the insufflation is 1-5 L/min.

7. A method of operating the insufflator for minimally invasive surgery according to claim 1 to establish a patient-specific pressure in a cavity, the method comprising the steps of:
a) presetting the at least one first set pressure in the electronic control unit of the insufflator;
b) initiating the gas flow into the cavity to begin a slow increase of pressure within the cavity towards the at least one first set pressure;
c) receiving an input from a user via the second input device, wherein the input is generated by the user at a moment when a desired expansion of the cavity is observed, said moment occurring during the slow increase of pressure and before the pressure in the cavity reaches the at least one first set pressure;
d) in direct response to receiving the input, automatically capturing the pressure prevailing in the body cavity at the moment the input is received;
e) setting the captured pressure as the second set pressure; and
f) maintaining the pressure in the body-cavity at the second set pressure for further insufflation.

* * * * *